United States Patent
Fischer et al.

(10) Patent No.: US 8,160,324 B2
(45) Date of Patent: Apr. 17, 2012

(54) ANALYZING IMAGE ERRORS

(75) Inventors: Axel Fischer, Wermsddorf (DE); Hermann-Josef Krämer, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 812 days.

(21) Appl. No.: 12/232,286

(22) Filed: Sep. 11, 2008

(65) Prior Publication Data
US 2009/0074273 A1    Mar. 19, 2009

(30) Foreign Application Priority Data
Sep. 19, 2007 (DE) .......................... 10 2007 044 631

(51) Int. Cl.
*G06K 9/00* (2006.01)
(52) U.S. Cl. ...................................... 382/128
(58) Field of Classification Search ................ None
See application file for complete search history.

(56) References Cited

U.S. PATENT DOCUMENTS

| | | | |
|---|---|---|---|
| 6,876,819 B2 * | 4/2005 | Sawada et al. | 399/9 |
| 6,986,604 B2 * | 1/2006 | Sembritzki | 378/207 |
| 7,035,554 B2 * | 4/2006 | Sawada et al. | 399/9 |
| 2002/0091971 A1 * | 7/2002 | Sawada et al. | 714/46 |
| 2002/0112733 A1 * | 8/2002 | Miyauchi et al. | 600/408 |
| 2003/0101375 A1 * | 5/2003 | Hohn | 714/25 |
| 2005/0021373 A1 * | 1/2005 | Spahn | 705/2 |
| 2005/0047553 A1 * | 3/2005 | Sembritzki | 378/207 |
| 2005/0078082 A1 * | 4/2005 | Muralidharan et al. | 345/156 |
| 2005/0114180 A1 * | 5/2005 | Ploetz et al. | 705/2 |

FOREIGN PATENT DOCUMENTS

| | | |
|---|---|---|
| DE | 10 2004 049 402 A1 | 3/2005 |
| DE | 103 39 486 A1 | 5/2005 |

OTHER PUBLICATIONS

German Office Action dated Aug. 25, 2008 with English translation.

* cited by examiner

*Primary Examiner* — Jermele M Hollington
(74) *Attorney, Agent, or Firm* — Lempia Summerfield Katz LLC

(57) ABSTRACT

A method for analyzing image errors in an image dataset of a medical imaging device is provided. The method includes transmitting the image dataset to a central computing center, analyzing the image errors by a server of the computing center, determining a type of image error in the image dataset, and forwarding the image dataset to a service technician who is responsible for the type of image error determined in the image dataset.

15 Claims, 2 Drawing Sheets

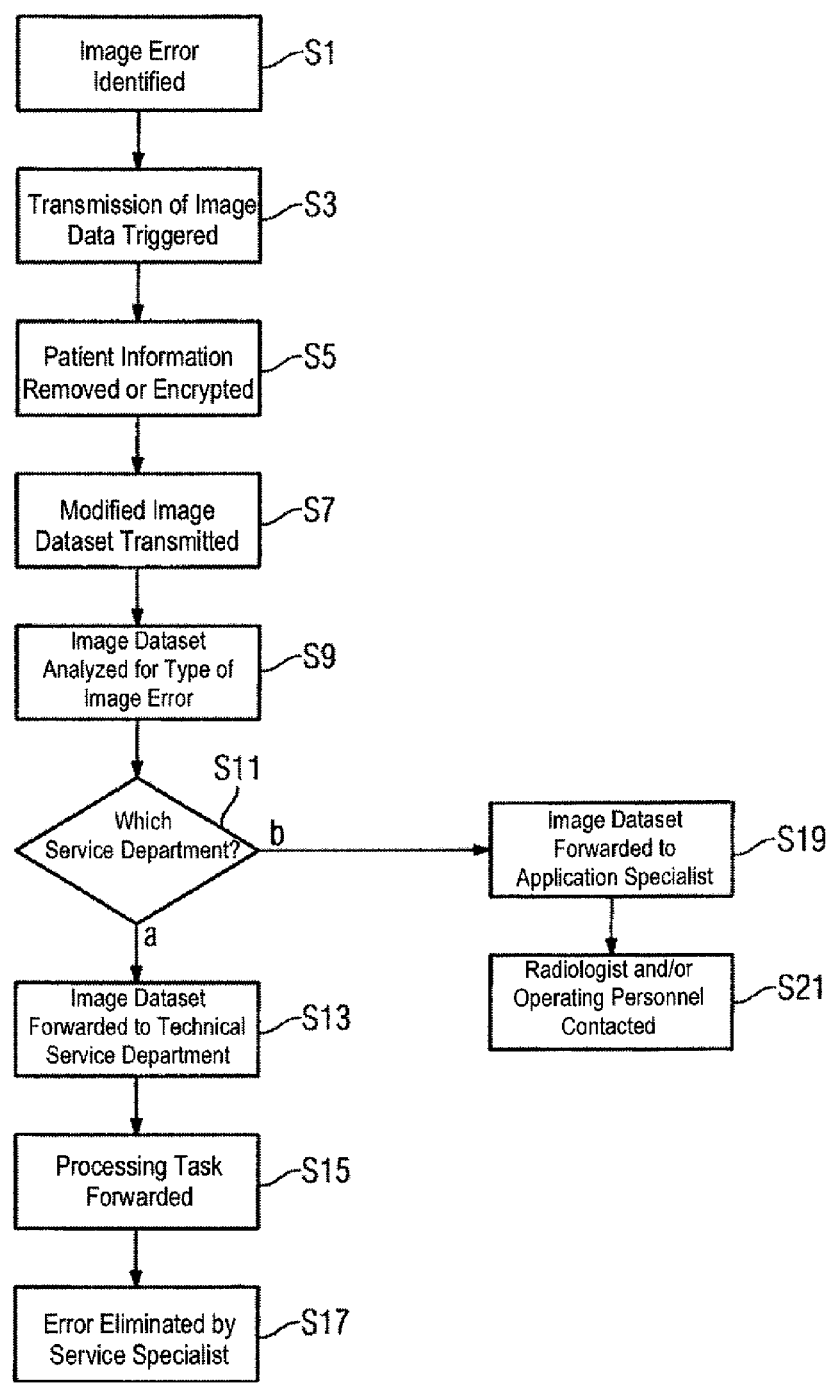

US 8,160,324 B2

ANALYZING IMAGE ERRORS

The present patent document claims the benefit of the filing date of DE 10 2007 044 631.6 filed on Sep. 19, 2007, which is hereby incorporated by reference.

BACKGROUND

The present embodiments relate to analyzing image errors in an image dataset of a medical imaging device.

Medical imaging modalities may be used to obtain medical images. Problems may arise with the image quality as a result of the complexity of the imaging operation or technology. Since there may be a plurality of causes for the resulting image errors, it may not be possible for an attending doctor or the operating personnel of the modality to solve the problem him/herself. For example, a magnetic resonance device may have a defective local coil, which may cause the image quality to reduce and lead to image errors. The image errors may occur as a result of a faulty operation of the magnetic resonance device. The complex interaction of the parameters to be adjusted complicate the operation and the achievement of an optimum image quality.

The doctor and/or operating personnel make a request for service from the manufacturer of the imaging modality. An image flawed with errors can, for instance, be sent to a service center by post on a CD or by e-mail. The image is analyzed manually by a service technician of the manufacturer of the imaging modality. The service technician identifies a plurality of sources for image errors and identifies the problems that lead to the image errors. Depending on whether this is a technical problem or an operating error, the service technician will forward the faulty file either to the application support or to the service support, where the respective fault source is then eliminated. In the case of operating errors, the doctor or operating personnel can attend a training course, or in the case of defects, a repair can take place by exchanging or repairing faulty parts. The method is lengthy and requires considerable personnel. Accordingly, the imaging modality may be used over a long period of time, however, not under optimum conditions for the image errors to be eliminated.

SUMMARY AND DESCRIPTION

The present embodiments may obviate one or more of the drawbacks or limitations inherent in the related art. For example, in one embodiment, an efficient method for analyzing image errors of an image dataset is provided.

In one embodiment, a method includes transmitting the image dataset to a central server, analyzing the image errors using the server, and forwarding the image dataset to a service technician who is responsible for the type of image errors according to the type of image error.

The automated analysis of the image errors in the image dataset by a central server dispenses with the need for a complicated manual analysis, which requires a large number of personnel, of the image material by an additional service technician.

BRIEF DESCRIPTION OF THE DRAWINGS

FIG. 2 illustrates one embodiment of a flowchart for analyzing image errors.

DETAILED DESCRIPTION

Figure 1:
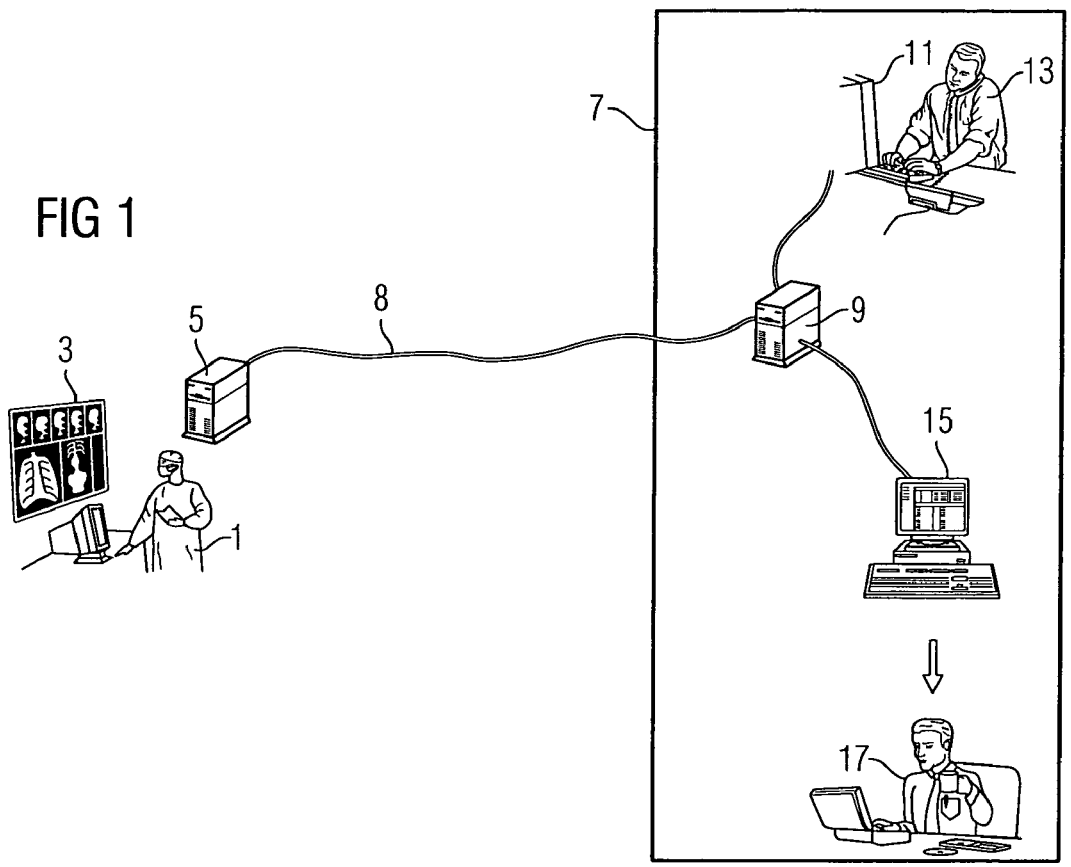
FIG. 1 illustrates one embodiment of a system for analyzing image errors.

FIG. 1 represents illustrates one embodiment of a system for analyzing image errors. A radiologist 1 evaluates image datasets 3 of a patient. The radiologist 1 uses a computer 5 to evaluate image datasets 3. The radiologist 1 determines image errors in the image dataset 3, the causes of which radiologist 1 is not able to identify. The radiologist 1 triggers a function by the evaluation software of the computer 5. The function forwards the image dataset 3 to a service center 7. The transmission of the image data is carried out by a network connection 8, for example, the Internet. The computer 5 provides the image dataset 3 with an identifier. The image dataset 3 in the service center 7 is automatically forwarded to an analysis computer 9. This can take place by an input computer.

The analysis computer 9 performs an analysis of the transmitted image dataset 3. The type of image errors which have occurred is analyzed. The analysis computer 9 identifies an error, which has occurred from a faulty operation by the radiologist 1 or the operating personnel, and the faulty image dataset 3 is forwarded to a terminal 11 of an application service technician 13. Information relating to the type of operating error, which is taken from the database, is conveyed to the application service technician 13 at the same time. The application service technician 13 contacts the radiologist 1 or the operating personnel of the imaging modality in order to eliminate the image error. Alternatively, a date can be agreed for a training course.

If the analysis computer 9 identifies a technical problem in the imaging modality as the cause of the image error, the image dataset 3 containing details relating to the causing technical defects is automatically forwarded to the service department, which is responsible for the faulty module. A processing task is generated on a central service computer 15 of the technical service department. The processing task may be transmitted to a service technician 17 who specializes in this problem. The service technician 17 can rectify the problem.

A repair may be carried out on site or by remote maintenance.

FIG. 2 shows a flowchart of one embodiment of analyzing image errors. In act S1, an image error is identified by a radiologist or an operating personnel or an imaging modality. In act S3, a transmission of the image data to a service center is triggered in the evaluation or operating software by the radiologist or operating personnel. In act S5, patient information, which is included in the image dataset, is removed or encrypted. The patient information may include, for example, name, date of birth and the patient ID. The image data is compressed and provided with an identifier, for example, at the same time. In act S7, the modified image dataset is transmitted to the service center by the Internet. An analysis of the image dataset, with respect to the type of image error, is performed by an evaluation computer on the basis of the identifier. Image quality problems may appear as a result of technically conditional artifacts, distortions, and missing image parts. The image quality problems may be false and inadequately optimized parameters for the image representation. Operating errors in the modality as a result of the service personnel may similarly have resulted in image errors.

In act S11, depending on the type of error that occurred, a decision is made as to which service department to forward the image dataset in order to eliminate the image error. In a first case (case a), a technical defect is present in the modality, as a result of which the image errors were produced. The image dataset is forwarded to the technical service department in act S13. At the same time, details relating to the expected causing defective module are transmitted to the service department. A processing task is initiated. In act S15, the processing task with the necessary information is forwarded to a responsible service specialist. In act S17, the service specialist eliminates the error, as a result of which the image errors no longer appear.

If it is determined in act S11 that an evaluation or operating error has resulted in the image errors (case b), the image dataset is forwarded to an application specialist in act S19. At the same time, details relating to the type of operating or evaluation error are conveyed to the application specialist. The application specialist contacts the radiologist and/or operating personnel in act S21 and will rectify the operating error so that the image errors can no longer occur and an optimum image quality can be achieved.

If further error sources and/or types are to still be identified by the analysis computer, further cases and a corresponding subsequent treatment of the image dataset are to be provided in act S11. When the analysis computer is not able to determine the error type or source, the image dataset is transmitted to a service employee who performs the analyses.

The analysis of the image dataset 3 can take place, for instance, by examining the pixels. Regions with identical image content may be found by a corresponding computer program. The computer program may indicate an error. The appearance of unexpectedly large content changes between adjacent pixels likewise indicates an image distortion.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A method for analyzing at least one image error in an image dataset of a medical imaging device, the method comprising:
    transmitting the image dataset to a central computing center;
    analyzing the at least one image error by a server of the central computing center;
    determining, by the server, a type of image error in the image dataset based on the analysis of the at least one image error; and
    forwarding, by the server, the image dataset to one of a first service technician and a second service technician based on the determination of the type of image error determined in the image dataset by the server.

2. The method as claimed in claim 1, wherein transmitting the image dataset includes encrypting the image dataset and transmitting the encrypted image dataset.

3. The method as claimed in claim 2, wherein patient data in the image dataset is made anonymous prior to transmitting the image dataset.

4. The method as claimed in claim 1, further comprising triggering the transmission of the image dataset by an operating personnel of the medical imaging device.

5. The method as claimed in claim 1, further comprising:
    adding an identifier to the image dataset prior to the transmission of the image dataset;
    transmitting the image dataset to an input server of the central computing center;
    checking the image dataset for the presence of the identifier; and
    transmitting the image dataset to the server.

6. The method as claimed in claim 1, further comprising identifying an image error.

7. The method as claimed in claim 6, wherein identifying an image error includes analyzing adjacent pixels to identify an appearance of unexpectedly large content changes between the adjacent pixels.

8. The method as claimed in claim 1, wherein analyzing includes examining pixels of the image dataset.

9. A method for analyzing image errors, the method comprising:
    identifying an image error in an image dataset;
    modifying the image dataset;
    transmitting the modified image dataset to a service center using the Internet;
    analyzing, by an evaluation computer of the service center, the image dataset to determine a type of image error;
    selecting, by the evaluation computer, a service department that eliminates the type of image error; and
    forwarding the image dataset to the selected service department.

10. The method as claimed in claim 9, wherein modifying includes removing or encrypting patient information in the image dataset.

11. The method as claimed in claim 10, wherein the patient information includes a name of a patient, a date of birth of the patient, a patient ID of the patient, or a combination thereof.

12. The method as claimed in claim 9, wherein modifying includes compressing the image dataset and providing the image dataset with an identifier.

13. The method as claimed in claim 9, wherein analyzing includes identifying artifacts, distortions, or missing image parts in the image dataset.

14. The method as claimed in claim 9, wherein selecting includes selecting a technical service department when the type of image error is a technical defect in the image dataset.

15. The method as claimed in claim 9, wherein selecting includes selecting an application specialist when the type of image error is an evaluation or operating error.

* * * * *